United States Patent [19]

Day et al.

[11] 4,372,776
[45] Feb. 8, 1983

[54] COMPOUNDS FOR THE LOOSENING OF FRUIT AND/OR LEAVES ON PLANTS

[75] Inventors: Janet A. Day, Sittingbourne; Robert J. G. Searle, Rodmersham Green near Sittingbourne, both of England

[73] Assignee: Shell Oil Company, Houston, Tex.

[21] Appl. No.: 312,039

[22] Filed: Oct. 16, 1981

[30] Foreign Application Priority Data

Nov. 5, 1980 [GB] United Kingdom ............... 8035442

[51] Int. Cl.³ .................... A01N 43/10; A01N 53/00; C07C 69/74; C07C 121/78
[52] U.S. Cl. .......................................... 71/90; 71/88; 71/105; 71/111; 260/465 D; 549/61; 549/65; 549/68; 549/76; 549/474; 549/475; 549/482; 549/494; 549/496; 560/21; 560/35; 560/45; 560/48
[58] Field of Search ............ 260/465 D; 560/19, 124, 560/35, 48; 549/76, 494, 496; 71/88, 90, 105, 111

[56] References Cited

FOREIGN PATENT DOCUMENTS 5782  5/1979  European Pat. Off. .

Primary Examiner—Dolph H. Torrence

[57] ABSTRACT

Compounds of the formula

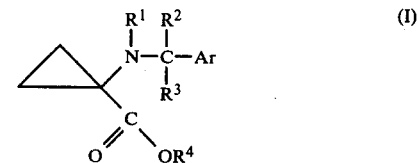

wherein $R^1$ and $R^3$ each is hydrogen or $R^1$ and $R^3$ together form a second carbon-to-nitrogen bond, $R^2$ is hydrogen or cyano, $R^4$ is alkyl and Ar is one of certain aromatic moieties.

The compounds can be used as abscission agents for the loosening of fruit and/or leaves on plants.

2 Claims, No Drawings

COMPOUNDS FOR THE LOOSENING OF FRUIT AND/OR LEAVES ON PLANTS

The invention relates to novel amino cyclopropylcarboxylic acid derivatives, to a process for the preparation thereof and to a method for the loosening of fruits and/or leaves on plants by a treatment with such derivatives or compositions thereof.

It is known that certain cycloalkanecarboxylic acid derivatives have plant growth regulating activity, which activity may relate to growth retardance, inhibition of sucker formation, defoliation, fruit loosening and the like. (cf European Patent Application No. 0,005,782). The cycloalkane moiety in these compounds may contain from 3–7 ring carbon atoms one of these being linked to a carbonyl group and to an amino, formamido, alkoylamino or aroylamino group.

It has now been found that certain aminocyclopropylcarboxylic acid derivatives which are believed to be novel compounds exhibit useful plant growth regulating properties; a number of them are suitable to be used as selective abscission agents. This is of advantage in the treatment of fruit bearing plants where it is generally intended to effect fruit loosening without causing substantial defoliation.

The invention can therefore be defined as relating to compounds of the general formula

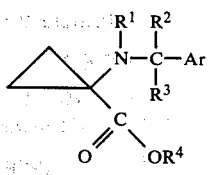

(I)

wherein $R^1$ and $R^3$ each is hydrogen or $R^1$ and $R^3$ together form a second carbon-to-nitrogen bond, $R^2$ is hydrogen or cyano, $R^4$ is alkyl of one to three carbon items, and Ar is thienyl, furyl, or phenyl optionally substituted by one or more of halogen, cyano, nitro, hydroxy, alkyl and alkoxy.

The invention further relates to a process for the preparation of compounds of formula (I). The process consists in reacting an aminocyclopropane compound of the formula

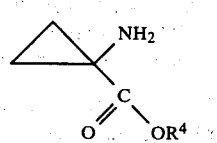

(II)

with a compound of the formula

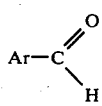

(III)

to form a compound of the formula

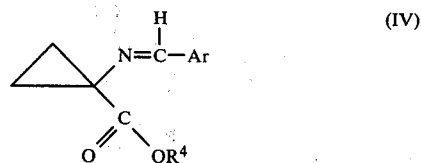

(IV)

$R^4$ and Ar having the meaning as defined above, which reaction is optionally followed by addition of a compound $HR^2$ and/or $HR^3$ to the —N=C< moiety in the compound of formula (IV) and further conversion to another compound of formula (I), $R^2$ and $R^3$ having the same individual meaning as defined above.

The reaction between a compound of formula (II) and a compound of formula (III) is conveniently performed at elevated temperature and in the presence of a solvent. Suitably an organic solvent, in particular an aromatic solvent is used, preferably toluene. The temperature is preferably selected such that water formed in the reaction is directly removed, preferably as an azeotrope with the solvent. Temperatures up to 150° C. are usually suitable. If a compound of the formula (I) is desired, in which a cyano group is linked to the carbon atom in the —N=C< moiety or in which the carbon atom attached to the Ar group is linked to the nitrogen atom by a single bond, the compound of formula (IV) has to be further converted. Thus for example a compound of formula (IV) may be converted into a compound of formula

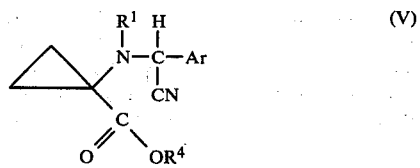

(V)

by reaction with a compound $R^1CN$ in which $R^1$ represent a hydrogen atom, an organic acyl group or a trialkylsilyl group. The reaction may be performed with HCN which may be generated in situ if desired, e.g. by the use of a cyanohydrin under alkaline conditions, or may be applied as such in the form of a gas or, preferably, a liquid. A preferred trialkylsilyl cyanide is trimethylsilylcyanide.

Suitable reaction temperatures are in the range of 0°–60° C. If HCN is used as cyanide reactant and prevailing temperatures are above 30° C., the reaction is suitably performed under superatmospheric pressures. A reaction solvent or a mixture of solvents may be used, recommended solvents being alcohols such as ethanol, dialkylethers, hydrocarbons or chlorinated hydrocarbons such as dichloromethane.

If desired the compounds of formula (V) may be converted into still other compounds of formula (I). These conversions may be effected according to methods analogous to those described in the art. For example a compound of formula (V) in which $R^1$ represents a hydrogen atom may be dehydrogenated with the aid of an oxidising agent such as manganese dioxide to form a compound of formula

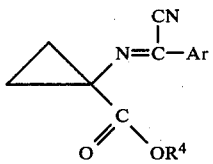

(VI)

The invention also provides a biologically active composition which comprises a novel compound according to the invention together with a suitable carrier. Preferably the amount of active ingredient in the composition is in the range of from 0.05 to 95% by weight of the composition.

A carrier in a composition according to the invention is any material with which the active ingredient is formulated to facilitate application to the plant to be treated or to facilitate storage, transport or handling. A carrier may be a solid or a liquid, including a material which is normally gaseous but which has been compressed to form a liquid, and any of the carriers normally used in formulating agricultural compositions may be used.

Suitable liquid carriers include alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils, chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution.

A surface-active agent may be an emulsifying agent, a dispersing agent or a wetting agent; it may be nonionic or ionic.

The compositions of the invention may for example be formulated as wettable powders, dusts, granules, solutions, emulsifiable concentrates, emulsions, suspension concentrates and aerosols. Wettable powders usually contain 25, 50 and 75% w of active ingredient and usually contain, in addition to solid inert carrier, 3–10% w of a dispersing agent and, where necessary, 0–10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½–10% w of active ingredient. Granules are usually prepared to have a size between 10 and 100 BS mesh (1.676–0.152 mm), and may be manufactured by agglomeration or impregnation techniques. Generally, granules will contain ½–25% w active ingredient and 0–10% w of additives such as stabilisers, slow release modifiers and binding agents. Emulsifiable concentrates usually contain, in addition to a solvent and, when necessary, co-solvent, 10–50% w/v of other additives such as stabilisers, penetrants and corrosion inhibitors. Suspension concentrates are usually compounded so as to obtain a stable, non-sedimenting flowable product and usually contain 10–75% w active ingredient, 0.5–15% w of dispersing agents, 0.1–10% w of suspending agents such as protective colloids and thixotropic agents, 0–10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation.

Aqueous dispersions and emulsions, for example compositions obtained by diluting a wettable powder or a concentrate according to the invention with water, also lie within the scope of the present invention. The said emulsions may be of the water-in-oil or of the oil in water type, and may have a thick 'mayonnaise'-like consistency.

The invention further relates to a method of loosening fruit and/or leaves on plants by treating the plant or part thereof with a compound of formula (I) or with a composition containing a compound of formula (I) as active ingredient, together with a suitable carrier.

The loosening of fruit within the meaning of the present specification includes the fall of fruit from the plant, as well as a reduction in strength of attachment of the fruit to the plant without actual fruit drop, which in some instances could cause damage to the fruit.

If selective loosening of fruit without substantial leaf abscission is envisaged a careful choice of the dosage of active compound to be applied in the loosening treatment is recommended. The optimal dosage will, inter alia, depend on the active compound, the nature and size of the plant to be treated and the period of time before harvesting. Generally dosages well below 20 g of active compound per plant are adequate and usually a dosage from 5 mg to 15 g active compound per plant is recommended.

The following Examples illustrate the invention:

EXAMPLE 1

Preparation of Ethyl N-Benzylidene-1-Amino-Cyclopropane Carboxylate (a) A solution of 1-amino cyclopropane carboxylic acid hydrochloride (7.2 g, 52 mM) in 500 ml ethanol was saturated with HCl and then stirred and heated under reflux for sixteen hours. Part of the ethanol was distilled off with the aid of a Dean Stark trap. More ethanol (200 ml) was added and the solution was again saturated with HCl. After heating for five hours the solvent was distilled off and the residue taken up in 300 ml CHCl$_3$. This solution was cooled to 0° C. and ammonia was bubbled through. Subsequently the solvent was evaporated from the suspension and the residue was taken up in diethylether (400 ml) and washed with water (20 ml). The product was extracted three times with diethylether (3×200 ml) and the combined ether solutions were dried over sodium sulphate and the ether was evaporated. The resulting ethyl 1-amino cyclopropane carboxylate was obtained in an amount of 4.0 g (60%).

(b) To a solution of ethyl 1-amino cyclopropane carboxylate (4.0 g) in 150 ml toluene, 3.29 g (0.03 M) benzaldehyde was added. The solution was stirred and heated under reflux using a Dean Stark trap for five hours. After standing for sixteen hours the solvent was evaporated. The desired product was obtained in a yield of 98% (6.62 g).

| Analysis: | C | H | N |
|---|---|---|---|
| Calculated for $C_{13}H_{15}NO_2$ | 71.9 | 7.0 | 6.5 |
| Found | 71.3 | 7.3 | 6.2 |

| Infra-red (cm$^{-1}$) | | 2980 | CH | strong |
|---|---|---|---|---|
| | | 1720 | C=O | strong |
| | | 1640 | C=N | strong |
| NMR | 8.3 ppm | singlet | | 1 H |
| (In CDCl$_3$) | 7.5 ppm | multiplet | | 5 H |
| | 4.1 ppm | quartet | | 2 H |
| | 1.6 ppm | triplet | | 2 H |
| | 1.2 ppm | multiplet | | 5 H |

EXAMPLE 2

Preparation of Ethyl N-(α-Cyanobenzyl)-1-Aminocyclopropane Carboxylate

Liquid HCN (2.4 ml; 0.062 M) was added to a solution of ethyl N-benzylidene-1-aminocyclopropane carboxylate (5.61 g, obtained as described in Example 1) in ethanol (25 ml) at room temperature. The solution was stirred at room temperature for forty eight hours; subsequently the excess ethanol was evaporated. The desired product was obtained in a yield of 100% (6.3 g).

| Analysis: | C | H | N |
|---|---|---|---|
| Calculated for C$_{14}$H$_{16}$N$_2$O$_2$ | 68.8 | 6.6 | 11.5 |
| Found | 69.3 | 6.7 | 11.3 |

| Infra-red (cm$^{-1}$) | | 3330 | N—H | strong |
|---|---|---|---|---|
| | | 2980 | C—H | strong |
| | | 2230 | C≡N | strong |
| | | 1720 | C=O | strong |
| NMR | 7.3 ppm | multiplet | | 5 H |
| (In CDCl$_3$) | 4.9 ppm | singlet | | 1 H |
| | 4.1 ppm | quartet | | 2 H |
| | 2.5 ppm | singlet | | 1 H |
| | 1.2 ppm | multiplet | | 7 H |

EXAMPLE 3

Preparation of Ethyl N-(α-Cyanobenzylidene)-1-Aminocyclopropane Carboxylate

Active manganese dioxide (4 g) was added to a solution of ethyl N-(α-cyanobenzyl)-1-aminocyclopropane carboxylate (2.0 g obtained as described in Example 2) in dry benzene (70 ml). The suspension was stirred at room temperature for sixteen hours. After filtration the solvent was evaporated.

The remaining liquid was dissolved in benzene (70 ml) and MnO$_2$ (4 g) was added. The suspension was stirred at room temperature for sixteen hours. After filtration the solvent was evaporated. Again the residue was taken up in benzene (70 ml) and MnO$_2$ (6 g) added. The suspension was stirred at room temperature for sixty four hours. After filtration and evaporation of the solvent, the desired product was obtained in a yield of 53% (1.05 g).

| Analysis: | C | H | N |
|---|---|---|---|
| Calculated for C$_{14}$H$_{14}$N$_2$O$_2$ | 69.4 | 5.8 | 11.5 |
| Found | 69.4 | 6.0 | 10.9 |
| Infra-red (cm$^{-1}$) | 3060 | C—H | strong |
| | 3030 | C—H | strong |
| | 2980 | C—H | strong |
| | 2220 | C≡N | strong |
| | 1725 | C=O | strong |
| | 1595 | C=N | strong |
| | 1575 | C=N | strong |
| NMR | 1.2 ppm | triplet | 3 H |
| | 1.3 ppm | multiplet | 2 H |
| | 1.8 ppm | multiplet | 2 H |
| | 4.2 ppm | quartet | 2 H |
| | 7.6 ppm | multiplet | 5 H |

EXAMPLES 4 to 14

By methods directly analogous to those described in Examples 1 to 3, further compounds of the general formula I were prepared. Details are given in Table I.

TABLE I

| Example No. | Meaning of symbols in the general formula I | | | | | Elemental analysis | | | | | |
|---|---|---|---|---|---|---|---|---|---|---|---|
| | | | | | | Calculated | | | Found | | |
| | R$^1$ | R$^3$ | R$^2$ | R$^4$ | Ar | C | H | N | C | H | N |
| 4 | bond | | H | —OC$_2$H$_5$ | 4-Cl—phenyl | 62.0 | 5.6 | 5.6 | 60.8 | 5.6 | 5.6 |
| 5 | H | H | CN | —OC$_2$H$_5$ | 2-thienyl | 57.6 | 5.6 | 11.2 | 57.4 | 5.7 | 11.2 |
| 6 | H | H | CN | —OC$_2$H$_5$ | 4-Cl—phenyl | 60.3 | 5.4 | 10.0 | 60.4 | 5.8 | 9.5 |
| 7 | bond | | CN | —OC$_2$H$_5$ | 2-thienyl | 58.1 | 4.8 | 11.3 | 58.2 | 4.9 | 11.4 |
| 8 | bond | | CN | —OC$_2$H$_5$ | 4-Cl—phenyl | 60.8 | 4.7 | 10.1 | 60.6 | 5.5 | 9.5 |
| 9 | bond | | H | —OC$_2$H$_5$ | 2-furyl | 63.8 | 6.3 | 6.8 | 63.9 | 6.5 | 6.8 |
| 10 | bond | | H | —OC$_2$H$_5$ | 3-thienyl | 59.2 | 5.8 | 6.3 | 59.1 | 5.9 | 6.3 |
| 11 | H | H | CN | —OC$_2$H$_5$ | 2-furyl | 61.5 | 6.0 | 11.9 | 60.8 | 6.0 | 11.6 |
| 12 | H | H | CN | —OC$_2$H$_5$ | 3-thienyl | 57.6 | 5.6 | 11.2 | 57.4 | 5.8 | 11.0 |
| 13 | bond | | CN | —OC$_2$H$_5$ | 2-furyl | 62.0 | 5.2 | 12.0 | 61.6 | 5.2 | 11.3 |
| 14 | bond | | CN | —OC$_2$H$_5$ | 3-thienyl | 58.1 | 4.8 | 11.3 | 57.9 | 5.2 | 10.6 |

EXAMPLE 15

Determination of the Abscission Activity

In a laboratory test, carried out to investigate the abscission activity of various compounds, the following procedure was used:-

French bean (cv. Canadian Wonder) were used as the indicator species for abscission activity. French bean seeds were sown at the rate of 2 per 8 cm pot in sterilized loam. Plants were maintained at 20° C. under 14 hours of daylight and watered by subirrigation. At the first trifoliate leaf stage of development, the laminae of the primary leaves were removed. Forty eight hours after removal of the laminae, liquid formulations of the test compounds were applied. The formulation used, consisted of 90% water and 10% acetone which contained 0.4% TRITON X155 (Trade Mark) and amounts of the test compound to give spray application at various dosages up to 2000 ppm.

Treatments were as foliar applications to "run off" using a fixed nozzle. After treatment the plants were set out in randomised block design. Results are given in Table II, in which 0 represents same as control; + represents greater than control; ++ represents much greater than control; and +++ represents a high level of abscission.

TABLE II

| Compound of Example No. | Abscission at given dosage (ppm) | | | |
| --- | --- | --- | --- | --- |
| | 50 | 250 | 1000 | 2000 |
| 1 | 0 | + | +++ | +++ |
| 2 | 0 | +++ | +++ | +++ |
| 3 | 0 | + | +++ | +++ |
| 4 | + | ++ | +++ | +++ |
| 5 | ++ | +++ | +++ | |
| 6 | + | ++ | +++ | |
| 7 | ++ | +++ | +++ | |
| 8 | + | + | +++ | |

COMPARISON EXAMPLE 16

In the same test as described for Example 15, compounds not within the scope of this invention scored as shown in Table III.

TABLE III

| Compound | Abscission at given dosage (ppm) | | | |
| --- | --- | --- | --- | --- |
| | 50 | 250 | 1000 | 2000 |
|  | 0 | + | ++ | +++ |
|  | 0 | 0 | 0 | |

EXAMPLE 17

Abscission Activity on Olives

Olive trees variety "Picual" were used in this test. Test branches bearing up to 100 olives were selected. Test solutions were made up containing 500 ppm of compound in a 50/50 volume/volume acetone/water solution with 0.05% Nonidet p40 (Trade Mark), a surfactant, added. 500 mls of each solution were applied to the test branch. Each test was carried out in triplicate. Control branches were sprayed with acetone/water/Nonidet p40 solution. In addition, tests were carried out using the commercial compound Etacelasil: this is a commercial olive abscission agent having the chemical formula $(CH_3.O.CH_2.CH_2.O)_3.Si.CH_2.CH_2.Cl$.

Five days after treatment, the strength of attachment of the olives to the branch was measured. The results are given in Table IV. This fruit retaining force is measured for a total of 25 olives. It can be seen from Table IV that olives treated with compounds according to the invention were attached to the branch much less strongly than the control fruit, and also less strongly than olives treated with the commercial compound Elacelasil.

TABLE IV

| Compound tested | Fruit retaining force (g) for 25 olives |
| --- | --- |
| Compound of Example 1 | 240.7 |
| Compound of Example 2 | 217.7 |
| Compound of Example 3 | 282.3 |
| Control group | 477.3 |
| "Etacelasil" (comparison) | 388.7 |

We claim:

1. A compound of the formula

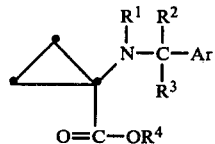

wherein $R^1$ and $R^3$ each is hydrogen or together form a second carbon-to-nitrogen bond, $R^2$ is hydrogen or cyano, $R^4$ is alkyl of one to three carbon atoms, and Ar is thienyl, furyl, or phenyl optionally substituted by one or more of halogen, cyano, nitro, hydroxy, alkyl or alkoxy.

2. A method for loosening fruit and/or leaves on a plant, comprising applying to the plant or part thereof an effective amount of a compound of claim 1.

* * * * *